(12) United States Patent
Chen et al.

(10) Patent No.: US 8,285,368 B2
(45) Date of Patent: Oct. 9, 2012

(54) ENDOSCOPIC LONG RANGE FOURIER DOMAIN OPTICAL COHERENCE TOMOGRAPHY (LR-FD-OCT)

(75) Inventors: Zhongping Chen, Irvine, CA (US); Jun Zhang, Irvine, CA (US); Matthew Brenner, Irvine, CA (US)

(73) Assignee: The Regents of the University of California, Oakland, CA (US)

( * ) Notice: Subject to any disclaimer, the term of this patent is extended or adjusted under 35 U.S.C. 154(b) by 201 days.

(21) Appl. No.: 12/833,717

(22) Filed: Jul. 9, 2010

(65) Prior Publication Data

US 2011/0009752 A1    Jan. 13, 2011

Related U.S. Application Data

(60) Provisional application No. 61/224,663, filed on Jul. 10, 2009.

(51) Int. Cl.
*A61B 6/00* (2006.01)
*A61B 1/00* (2006.01)
(52) U.S. Cl. .................................. 600/478; 600/101
(58) Field of Classification Search .............. 600/101, 600/118, 162, 476, 478; 359/340
See application file for complete search history.

(56) References Cited

U.S. PATENT DOCUMENTS

| 7,261,687 | B2 * | 8/2007 | Yang .............................. 600/173 |
| 2009/0174931 | A1 * | 7/2009 | Huber et al. ................... 359/340 |

OTHER PUBLICATIONS

"Quantitative Upper Airway Imaging with Anatomic Optical Coherence Tomography", Armstrong et al, Am J Respir Crit Care Med vol. 173. pp. 226-233, 2006.*

* cited by examiner

*Primary Examiner* — Michael Rozanski
(74) *Attorney, Agent, or Firm* — Marcus C. Dawes; Daniel L. Dawes

(57) ABSTRACT

An endoscopic swept-source Fourier Domain optical coherence tomographic system (FDOCT system) for imaging of tissue structure includes a Fourier Domain mode locked (FDML), high speed, narrow line-width, wavelength swept source, an OCT interferometer having a sample arm, a reference arm, a detection arm, and a source arm coupled to the swept source, an endoscopic probe coupled to the sample arm, and a data processing circuit coupled to the detection arm. The swept source includes a long optic fiber functioning as a cavity, a high optical gain lasing module, and a tunable narrow bandwidth bandpass filter for wavelength selection combined to form a unidirectional ring laser cavity, where the tunable narrow bandwidth bandpass filter is driven synchronously with the optical round-trip time of a propagating light wave in the cavity.

15 Claims, 9 Drawing Sheets

|  | 1 CORE | 2 CORES | 3 CORES | 4 CORES |
|---|---|---|---|---|
| 32 BIT | 4.82 | 2.58 | 1.78 | 1.37 |
| 64 BIT | 9.23 | 4.88 | 3.31 | 2.575 |

ENDOSCOPIC LONG RANGE FOURIER DOMAIN OPTICAL COHERENCE TOMOGRAPHY (LR-FD-OCT)

RELATED APPLICATIONS

The present application is related to U.S. Provisional Patent Application Ser. No. 61/224,663, filed on Jul. 10, 2009, which is incorporated herein by reference and to which priority is claimed pursuant to 35 USC 119.

BACKGROUND OF THE INVENTION

1. Field of the Invention
The invention relates to the field of
2. Description of the Prior Art
There are approximately 20-40 million people in the United States with sleep apnea. The majority of them are undiagnosed and untreated at this time. Sleep apnea can lead to severe health complications including hypertension, heart failure, memory impairment, motor vehicle and work accidents, decreased work productivity, and increased risk of death. The diagnosis and management of sleep apnea currently requires polysomnography, which is complex, time-consuming; expensive, and of limited availability. The development of a novel, simple, rapid, minimally invasive method for the diagnosis and optimization of treatment of patients with obstructive sleep apnea would be a tremendous advance for these millions of patients.

In the last twenty-five years, obstructive sleep apnea has been recognized as a very common disorder and an important cause of morbidity and mortality. Obstructive sleep apnea is characterized by repetitive interruptions of breathing during sleep due to the collapse of the upper airway. The cessation of airflow usually lasts 10 seconds or more, which is defined as apnea. While 24% of males and 9% of females have 5 or more apneas per hour, the prevalence of more severe forms (more than 15 apneas per hour) has been shown to be 12% in men and 5% in women. Airway obstruction during sleep may occur at one or more sites in areas of the nasopharynx, oropharynx and hypopharynx. For the majority of patients with obstructive sleep apnea, airway closure occurs most commonly in the oropharynx region.

The abnormalities may take the form of steady snoring, protracted hypopneas with intermittent arousals or self-perpetuating transient obstructive events that recur over minutes, hours, or the entire sleep time. Frequently, these various manifestations occur in the same individual at different times. Due to repetitive cycles of snoring, airway collapse, and arousal, patients with obstructive sleep apnea suffer from fragmented sleep, chronic fatigue, daytime sleepiness, lack of concentration, and memory problems. The wide range of consequences of obstructive sleep apnea include hypertension, impotence, increased risk of motor vehicle accidents and the development of cardiovascular diseases such as right and left ventricular failure, myocardial infarction, and stroke.

The current diagnostic gold standard is in-laboratory, full overnight polysomnography which is performed to confirm the presence of upper airway closure during sleep and to assess the patient's level of risk. The polysomnogram study consists of recordings of arterial oximetry, respiratory effort, naso-oral airflow, snoring, electrocardiography and of neurophysiological variables including electroencephalogram (EEG), bilateral electro-oculogram (EOG), submental electromyogram (EMG), and bilateral anterior tibialis EMG for diagnosis of obstructive sleep apnea. Unfortunately full sleep studies are expensive, inconvenient and unable to localize and map the upper airway obstruction sites in obstructive sleep apnea patients which is important in choosing the appropriate treatment, especially for surgical intervention.

Nasal continuous Positive Airway Pressure (CPAP) treatment is the most effective and widely used method for treating obstructive sleep apnea. Through the use of a snugly fitting nasal mask, CPAP provides a gentle flow of positive pressure air to keep the airway open during sleep. The optimal titrated pressure which is the air pressure just high enough to prevent most apneas and hypopneas is determined after review of overnight comprehensive polysomnography study with progressively increasing airway pressures supervised by a sleep technician in a sleep laboratory. A lack of response to the conservative treatment qualifies a patient for surgical correction of the offending anatomical site in obstructive sleep apnea. The obstructed tissue is removed or shrunken to increase the size of the upper airway thereby preventing collapse of the airway and making breathing easier:

Our understanding of the human in-vivo upper airways activity during normal breathing and especially in sleep disordered breathing is limited. Upper airway imaging techniques routinely used include endoscopy, nuclear magnetic resonance imaging (MRI), computed tomography (CT), X-ray cephalometry, acoustic reflection, and fluoroscopy. However, X-ray cephalometry, CT and fluoroscopy all involve exposure to potentially hazardous radiation. MRI is cumbersome, expensive, noisy, claustrophobic and even impossible for patients who have contraindications to MRI. As a result, X-ray cephalometry, CT, MRI and fluoroscopy are impractical for continuous overnight studies.

Endoscopy is not associated with radiation but it requires subjective visual outlining of the airway wall for evaluation of the upper airway dimensions. Acoustic reflection is noninvasive, however it can be only performed in the sitting, instead of the supine, position, and is incapable of high resolution anatomical imaging. Due to these limitations, current upper airway imaging methods are unable to confirm or exclude obstructive sleep apnea with adequate sensitivity and specificity and therefore are not part of the routine diagnostic evaluation for obstructive sleep apnea.

Research advances with OCT have been widely used in opthalmology and dermatology. The first in-vivo endoscopic OCT images in animals and humans were reported in 1997. Thereafter endoscopic OCT has been rapidly developed for intravascular accessing and imaging of respiratory, urogenital, and GI tracts. OCT takes advantage of the short coherence length of broadband light sources to perform high resolution (about 10 μm), high sensitivity (about 100 dB), cross-sectional imaging of biological tissues. It is analogous to ultrasound B-mode imaging, but uses laser light reflectance, rather than sound as its basis. In OCT, light is emitted from a low coherence source and coupled to an interferometer where the light is split into two paths. The laser light from the low coherence source is emitted over a broad range of wavelengths that is defined by the coherence length. After being split, one beam is directed toward the sample material and the other to a reference mirror. Light backscattered by the sample is recombined with reflected light from the reference mirror to produce an interference pattern only for coherent photons that have an optical path length difference between reference and target that matches to within the source coherence length (10 μm). Hence, the recorded interference signal at the photodetector corresponds to a specific depth within the test material and results in high axial spatial resolution.

To perform depth scans in time domain OCT systems, the reference arm length is progressively increased by moving a reference mirror. Moving the scanning mechanism laterally (or rotationally) across the sample produces two-dimensional and three dimensional images. The coherence length of the light source determines the axial resolution of the system, while the lateral resolution is determined by the optical design of sampling probe or catheter.

Optical coherence tomography (OCT) is an imaging modality to perform cross section view. OCT is analogous to ultrasound except that imaging is performed with light instead of acoustic waves. OCT is non invasive and non ionizing allowing study over lengthy periods during both sleep and wakefulness. Conventional OCT which is based on time domain technique has very limited imaging speed which precludes its use in real-time, dynamic monitoring and large volume detection.

OCT systems have also been described, that through manipulation of the rapid scanning optical delay (RSOD) line configurations, can provide longer range OCT images with larger scale quantitative information about the lumen size, and shape of the upper airway. These systems can produce anatomical upper airway images with minimal invasiveness allowing study over lengthy periods during both sleep and wakefulness, and have shown the potential for studies of airway collapse during sleep apnea. However, the reported studies use time domain (TD) techniques with limited speed and sensitivity and can only achieve an imaging speed of less than 3 frames per second—which precludes its use in real-time, dynamic monitoring and large volume detection such as three dimensional imaging over the entire upper airway. In addition, motion artifacts of the airway during respiration would result in image blurring in low speed systems.

The demonstrated TDOCT systems can produce anatomical upper airway images with minimal invasiveness allowing study over lengthy periods during both sleep and wakefulness, and have shown the potential for studies of airway collapse during sleep apnea. However, the reported studies use time domain techniques with limited speed and sensitivity and can only achieve an imaging speed of less than 3 frames per second—which precludes its use in real-time, dynamic monitoring and large volume detection such as three dimensional imaging over the entire upper airway. In addition, motion artifacts of the airway during respiration would result in image blurring in low speed systems For example, J. J. Armstrong et. al., "Quantitative upper airway imaging with anatomic optical coherence tomography", Amer. J. Respir. Crit. Care Med., 2006. 173: p. 226-323, discloses a time domain optical coherence tomography (TDOCT) system that can provide long range OCT images with large scale quantitative information about the lumen size, and shape of the upper airway through manipulation of the rapid scanning optical delay (RSOD) line configurations.

BRIEF SUMMARY OF THE INVENTION

An alternative OCT technique to time domain OCT is Fourier domain OCT (FDOCT). FDOCT is characterized by higher speed and sensitivity and the elimination of depth scanning. Two methods have been developed to employ the Fourier domain technique: FDOCT using a spectrometer with a line-scan camera, and FDOCT using a rapidly wavelength swept laser source as disclosed below.

To achieve the long imaging range necessary for full upper airway anatomical imaging, a much narrower spectral linewidth is required with a FDOCT system. This narrow spectral resolution is very difficult to achieve for a spectrometer FDOCT system to achieve due to limited spectrometer fidelity and cross talk between pixels of a line scan camera. Swept-source FDOCT has the advantages of a simple system design since no spectrometer is required. A long imaging range can be achieved by designing a swept-source with a narrow spectral line-width and without crosstalk.

The technique of the illustrated embodiment includes the step of combing a narrow line-width swept-source based FDOCT system with an endoscopic probe to enable an ideal upper airway imaging technology which is low-cost, compact, noninvasive, non-ionizing, dynamic (to visualize apneic events), suitable for supine position study, and capable of high resolution three dimensional images. This technology provides a mechanism for dynamic evaluation of obstructive sleep apnea.

The illustrated embodiment of the invention uses a Fourier domain technique based on a narrow bandwidth high speed wavelength swept source and provides much higher imaging speed compared to the previous time domain method. The new technique is capable of long-range, ultra-fast, high sensitivity, three-dimensional, quantitative and continuous imaging of the upper airway anatomy.

An endoscopic long range Fourier domain optical coherence tomography (LR-FD-OCT) system permits the rapid three-dimensional anatomical imaging of airways and provide a mechanism for determining the sites and extent of airway collapse during obstructive sleep apnea.

The illustrated embodiment show four methods and types of apparatus to implement high speed narrow bandwidth wavelength swept sources:
 a. Fourier Domain mode locked (FDML), high speed narrow bandwidth wavelength swept source using long fiber/FDML;
 b. High speed narrow bandwidth wavelength swept source based on a Fabry-Pérot (FP) tunable filter and Wavelength-division multiplexing (WDM) couplers using long fiber/FDML;
 c. High speed narrow bandwidth wavelength swept source based on a short cavity; and
 d. High speed narrow bandwidth wavelength swept source based on a frequency shifter using short fiber.

For example, in the illustrated embodiments, the endoscopic swept-source Fourier Domain optical coherence tomographic system (FDOCT system) for imaging of tissue structure includes a Fourier Domain mode locked (FDML), high speed, narrow line-width, wavelength swept source, an OCT interferometer having a sample arm, a reference arm, a detection arm, and a source arm coupled to the swept source, an endoscopic probe coupled to the sample arm, and a data processing circuit coupled to the detection arm.

The swept source includes a long optic fiber functioning as a cavity, a high optical gain lasing module, and a tunable narrow bandwidth bandpass filter for wavelength selection combined to form a unidirectional ring laser cavity, where the tunable narrow bandwidth bandpass filter is driven synchronously with the optical round-trip time of a propagating light wave in the cavity.

In one embodiment, the long single mode optic fiber is equal or greater than 100 m in length, but in another embodiment the long single mode optic fiber is equal or greater than 1 km in length.

The gain module includes a semiconductor optical amplifier, doped fiber, or gain medium with lasing originated from nonlinear effects.

The FDOCT system further includes a plurality of polarization controllers in optical circuit in cavity.

The wavelength tuning is implemented with a fiber Fabry-Pérot tunable filter, a galvanometer based tunable filter, a microelectromechanical systems (MEMS) based tunable filter, or a tunable filter based on non-mechanical tuning mechanism such as electro-optic and acousto-optic (AO) filters, or spatially dispersed broadband pulses.

The swept source is arranged and configured to operate in a quasi-stationary regime.

The swept source has a center frequency adjusted to the zero dispersion point of the optical fiber by tuning the bias voltage of the filter driven signal, where the tuning range of the filter is set to less than 80 nm by using a gain medium with a predetermined spectrum relative to the bandwidth response of the tunable filter, and arranging and configuring the tunable filter to have a line width of not more than approximately 0.03 nm.

In another embodiment, the swept source includes a short cavity, a high gain module, a tunable narrow bandwidth bandpass filter and a reflector and a partial reflector combined to form a short optical cavity laser.

A small fraction of the laser output is tapped out and propagated through an interferometer such as a Faby-Perot interferometer, a Mach-Zehnder interferometer or a Michelson interferometer, etc to generate a multi-wavelength reference for dynamic calibration of the swept spectra that is essential for rigorous conversion from time to wavenumber space.

A wavelength filter such as a fiber Bragg grating (FBG) configured in parallel is used as a wavelength marker to generate a wavelength reference signal to stabilize the swept spectrum. The feedback signal will be used to control and maintain the tunable filter and thus wavelength repeatability.

In another embodiment, the tunable filter operates in a multi-band mode by simultaneously filtering two or more wavelengths at different spectral bands so that the swept source has an output comprised of multi wavelengths within different spectral bands. The FDOCT system further includes at least two wavelength-division multiplexing (WDM) couplers in optical circuit in the detection arm of the OCT interferometer, where the WDM couplers pass-band match the spectral bands of the filter and where the OCT interferometer divides the spectral bands into separate channels for detection.

In another embodiment, the swept source incorporates a high gain module, a single mode fiber coil, a tunable narrow bandwidth bandpass filter, a frequency shifter and the associated optical isolators and couplers to form a unidirectional ring laser. The shifted frequency generated by the frequency shifter is chosen to be identical to the scanned frequency of the tunable filter over the round-trip time of light in the cavity. The laser modes working at the peak wavelength of the filter will always experience the minimum loss as the filter is scanned and can travel many round trip cycles in the cavity. Hence the line-width of the light is significantly narrowed.

The endoscopic probe includes a hollow elongate flexible sheath with a distal and proximal end, an optic fiber extending from the proximal toward the distal end of the sheath, a gradient index (GRIN) lens coupled to the optic fiber, a MEMS motor proximately disposed within the distal end of the elongate sheath and backwardly mounted at the distal end of the sheath and having an output shaft, a controller coupled to the motor, a flexible control wire coupling the motor and controller extending through the sheath from its proximal end to the motor, and a mirror coupled to the output shaft of the motor to reflect the beam which is focused by the GRIN lens toward the mirror and thence to the tissue structure being sampled.

The FDOCT system further includes a glass rod spacer disposed between the optic fiber and the GRIN lens to reduce reflection from the surface of the GRIN lens.

The FDOCT system further includes a translational stage coupled to the sheath to provide precisely controlled longitudinal displacement of the sheath.

The GRIN lens is arranged and configured to have a long focal length so that the probe imaging range is at least from 3 mm to 30 mm within which a working distance lies.

The glass rod spacer has a length and where the working distance of the probe and its focal spot is precisely tunable by adjusting the length of the glass rod spacer.

The scope of the invention also contemplates inclusion of the above endoscopic probe apart from the FDOCT system.

The scope of the invention further extends to include a method of using an endoscopic swept-source Fourier Domain optical coherence tomographic system (FDOCT system) for rapid three-dimensional anatomical imaging of an airway and for determining the site and extent of airway collapse during obstructive sleep apnea including the steps of providing a narrow line-width, wavelength swept source with a laser cavity, Fourier Domain mode locking (FDML) the narrow line-width, wavelength swept source, scanning the airway with an endoscopic probe coupled to an OCT interferometer using the swept source as a light source, and data processing the scanned signal to obtain an image of the airway to determine the site and extent of airway collapse during obstructive sleep apnea.

The step of Fourier Domain mode locking (FDML) the narrow line-width, wavelength swept source includes the step of synchronously driving a tunable narrow bandwidth bandpass filter in the cavity of the swept source with the optical round-trip time of a propagating light wave in the cavity.

The step of providing a narrow line-width, wavelength swept source with a laser cavity includes the step of operating the swept source in a quasi-stationary regime.

The swept source includes a tunable filter in the cavity, where the cavity is formed as a ring laser cavity using optical fiber coupled to a gain medium and the step of operating the swept source in a quasi-stationary regime includes the steps of adjusting a center frequency of the swept source to a zero dispersion point of a single mode optical fiber by tuning the bias voltage of the filter driven signal, and tuning the range of the filter to less than 80 nm by providing a gain medium with a predetermined spectrum relative to the bandwidth response of the tunable filter, and arranging and configuring the tunable filter to have a line width of not more than approximately 0.03 nm.

The method further includes the steps of deploying a multi-wavelength reference to stabilize the swept spectrum by using a feedback signal to control and maintain the tunable filter bias at a starting wavelength, and applying a scanning filter strategy based on a non-mechanical tuning mechanism.

While the apparatus and method has or will be described for the sake of grammatical fluidity with functional explanations, it is to be expressly understood that the claims, unless expressly formulated under 35 USC 112, are not to be construed as necessarily limited in any way by the construction of "means" or "steps" limitations, but are to be accorded the full scope of the meaning and equivalents of the definition provided by the claims under the judicial doctrine of equivalents, and in the case where the claims are expressly formulated under 35 USC 112 are to be accorded full statutory equivalents under 35 USC 112. The invention can be better visualized by turning now to the following drawings wherein like elements are referenced by like numerals.

BRIEF DESCRIPTION OF THE DRAWINGS

FIG. 6a shows one slice of the three dimensional OCT Images of human left lower lobe bronchus. FIG. 6b shows the three dimensional image reconstructed from 400 slices. The longitudinal length is 8 mm. The lesion at the inside wall can be clearly identified.

Figure 1:
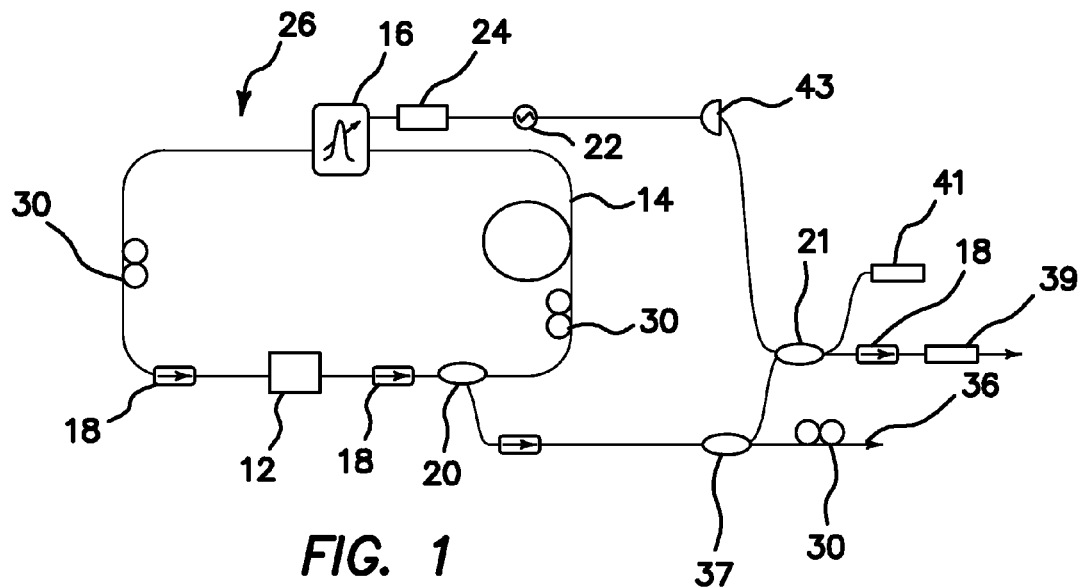
FIG. 1 is a schematic of a prototype setup of the narrow line-width swept-source based on long cavity, which demonstrates the feasibility and operability of the illustrated embodiments.

The invention and its various embodiments can now be better understood by turning to the following detailed description of the preferred embodiments which are presented as illustrated examples of the invention defined in the claims. It is expressly understood that the invention as defined by the claims may be broader than the illustrated embodiments described below.

DETAILED DESCRIPTION OF THE PREFERRED EMBODIMENTS

Fourier Domain OCT (FDOCT)

Fourier domain OCT (FDOCT) measures the magnitude and delay of backscattered light by spectral analysis of the interference pattern, can achieve a 50 to 500 fold increase in imaging speed and a much higher sensitivity compared to the TDOCT technique. Two methods have been developed to employ the Fourier domain technique: FDOCT using a spectrometer with a line-scan camera, and FDOCT using a rapidly wavelength swept laser source. One major limitation of FDOCT in long-range imaging is that the sensitivity and signal to noise ratio roll off with the increased depth. The imaging range of a FDOCT system is defined as the range with a sensitivity roll-off of less than 6 dB, which is typically several millimeters. This range is sufficient to acquire information about the structure and properties of tissue in which the penetration depth is limited to 2 to 3 mm by the absorption and scattering properties of the sample. However, determination of surface and subsurface structure and properties in large hollow organs such as the upper airway for sleep apnea evaluation requires a scanning range of several centimeters.

In FDOCT, the imaging range $\delta L$ is determined by the spectral line width $\delta \lambda$. and working wavelength $\lambda$ of the system as:

$$\delta L = \frac{2\ln 2}{\pi} \frac{\lambda^2}{\delta \lambda} \quad (1)$$

The typical line width of current FDOCT systems at a working wavelength of 1300 nm is around 0.2 nm corresponding to an imaging range of 3.7 mm. To achieve the long imaging range of 25 mm necessary for full upper airway anatomical imaging, a much narrower spectral line width of around 0.03 nm is required with a FDOCT system. This narrow spectral resolution is very difficult for a spectrometer FDOCT system due to limited spectrometer fidelity and cross talk between pixels of a line scan camera. Removal of the mirror image which accompanies the structural image due to Fourier transformation in FDOCT could double the limited imaging range. However, the procedure requires multiple A-line data to process, which reduces the imaging speed of a spectrometer FDOCT system.

Swept-source FDOCT has the advantages of a simple system design since no spectrometer is required. A long imaging range can be achieved by designing a swept-source with a narrow spectral line width and without crosstalk. In addition, we disclose a swept source FDOCT design that does not require multiple scans to remove mirror images and autocorrelation noise. Full range complex imaging can be obtained by using a phase modulator at the reference arm in the swept-source FDOCT system. The most important component in a swept-source FDOCT system is the swept light source. Currently, several commercial swept light sources have been reported (Micron Optics, Santec, and ThorLabs, etc.). These swept laser sources incorporate a semiconductor optical amplifier (SOA) gain medium with a tunable optical bandpass filter in the cavity, which have the drawbacks of broad line width (line width is more than 0.15 nm corresponding to an imaging range of 5 mm) and limited maximum achievable tuning rate (less than 28 kHz) due to the characteristic time constant for building up laser activity inside the cavity.

This limitation can be overcome with the Fourier Domain Mode Locking (FDML) technique by extending the laser cavity and periodically driving the optical bandpass filter synchronously with the optical round-trip time of the propagating light wave in the laser cavity. This permits broad sweep ranges and unprecedented sweep rates. In addition, narrow instantaneous line width is possible because FDML swept-source operates in a quasi-stationary regime. Despite its advantages there is no narrow line width swept-source currently available to provide enough imaging depth for upper airway anatomical imaging.

A number of technological advances enable us to develop a long-range, ultra-fast, high sensitivity, three-dimensional OCT system capable of imaging the upper airway anatomy quantitatively and continuously. These technological advances are described in more detail below, and include the development of a FDML based narrow line width swept-source, microelectromachined motor (MEMS-based technology) for probes, increased computing speed, and image construction capabilities. These technologies enable the potential of an ideal upper airway imaging technology which is low cost, compact, noninvasive, non-ionizing, dynamic (to visualize apneic events), suitable for supine position study, and capable of high resolution three dimensional images. Successful development of such an advanced system is expected to lead to the development of novel and innovative approaches to improve diagnosis and treatment of obstructive sleep apnea.

Swept Laser Based on FDML Techniques

We have designed and developed several high speed three dimensional MEMS based endoscopic swept-source FDOCT systems and applied the OCT technique on airway imaging of in-vitro excised tissues, in-vivo normal and pathologic animals, and human cases.

Figure 4:
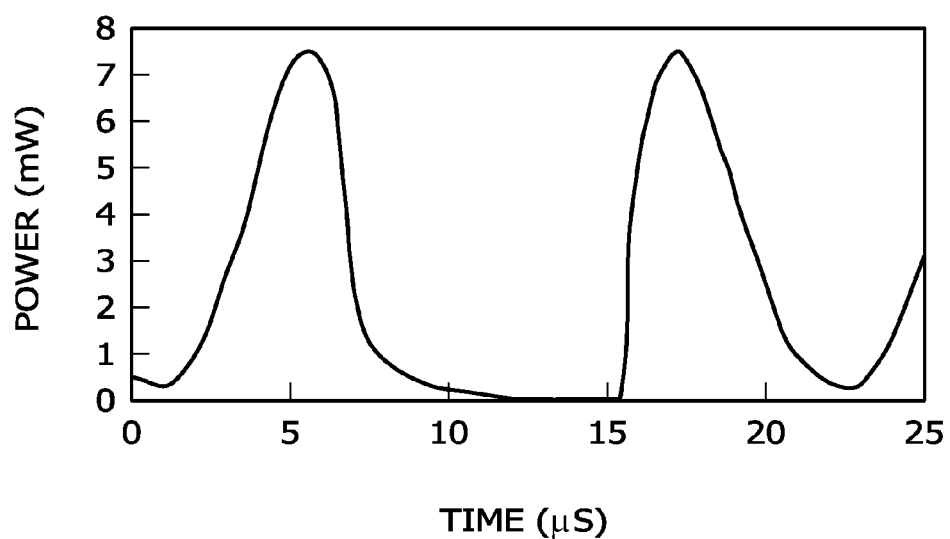
FIG. 4 is a graph of the temporal waveforms of the 1300 nm swept laser at 45.6 kHz sweep rate. Both forward and backward scanning are shown.
Figure 5:
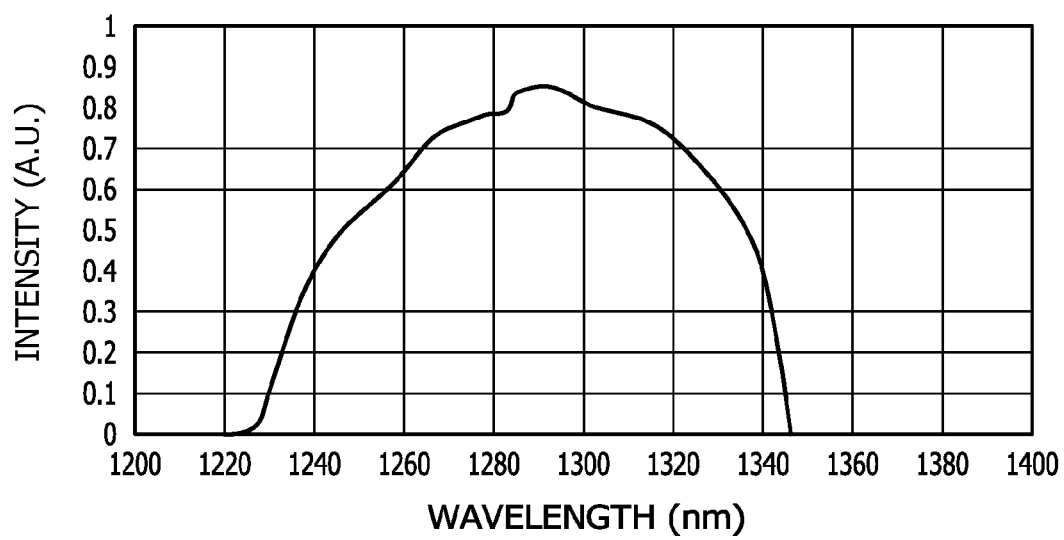
FIG. 5 is a graph of the spectrum of the swept laser at 45.6 kHz sweep rate measured with an optical spectrum analyzer in peak hold mode.

One embodiment of a high speed, narrow bandwidth or line-width, wavelength swept source 10 using a long fiber 14 as laser cavity 26 as shown in the schematic diagram of FIG. 1. The swept source 10 incorporates a high gain module 12, an optic fiber 14, a tunable narrow bandwidth bandpass filter 16 for wavelength selection and the associated optical isolators 18 and couplers 20 to form a unidirectional ring laser. The optical isolators 18 provide unidirectionality and prevent back reflections to enhance laser stability. The length of the single mode fiber optic fiber 14 is in the order of kilometers or several hundred meters and acts as a resonator. The gain module 12 can be a semiconductor optical amplifier (SOA), doped fiber, or gain medium with lasing originated from nonlinear effects. The typical nonlinear effects include stimulated Raman scattering (SRS), four wave mixing (FWM), or stimulated Brillouin scattering (SBS) etc. The wavelength tuning of filter 16 can be implemented with a fiber Fabry-Pérot tunable filter, a galvanometer based tunable filter, a microelectromechanical systems (MEMS) based tunable filter, or a tunable filter based on non-mechanical tuning mechanism such as electro-optic and acousto-optic AO filters, or spatially dispersed broadband pulses. The tunable filter 16 is driven by function generator 22 and amplifier 24 with a frequency which is synchronous to the round-trip time of light in the cavity 26. A plurality of polarization controllers 30 are included in optical circuit with the fiber 14 of cavity 26. A small fraction of the laser output is tapped out through coupler 37 in FIG. 1 and propagated through an interferometer 39 such as a Faby-Perot interferometer, a Mach-Zehnder interferometer or a Michelson interferometer, etc to generate a multi-wavelength reference for dynamic calibration of the swept spectra that is essential for rigorous conversion from time to wavenumber space. A wavelength filter such as a fiber Bragg grating (FBG) 41 configured in parallel through coupler 21 with interferometer 39 and is used as a wavelength marker to generate a wavelength reference signal to stabilize the swept spectrum. The feedback signal is provided to detector 43, whose output is fedback to function generator 22 to be used to control and maintain the tunable filter 16 and thus wavelength repeatability. FIGS. 4 and 5 show the temporal profile and spectrum of the swept laser 10, at a sweep rate of 45.6 kHz, respectively. The peak power of the laser is 7.5 mW and the full width half maximum (FWHM) bandwidth is 99 nm.

Thus, it can be appreciated that FIG. 1 shows an apparatus and method for: 1) deploying a multi-wavelength reference for spectral calibration by using a Fabry-Perot interferometer, a Mach-Zehnder interferometer or a Michelson interferometer 39, etc to exhibit uniformly spaced resonance frequency combs; 2) applying a wavelength reference to stabilize the swept spectrum by using a wavelength marker detected by a wavelength filter such as a fiber Bragg grating 41 and using feedback signal to control and maintain the tunable filter 16 and thus wavelength repeatability; and 3) applying a scanning filter strategy using non-mechanical tuning mechanisms such as electro-optic and acousto-optic (AO) filters (not shown) controlled by drivers or function generators, or using spatially dispersed broadband pulses. The scanning filter strategy using spatially dispersed broadband pulses is conventional and detailed examples can be found in Sucbei Moon and Dug Young Kim, "Ultra-high-speed optical coherence tomography with a stretched pulse supercontinuum source," Opt. Express 14, 11575-11584 (2006). However, the application of the strategy in the present context is novel. In other words, a stretched pulse supercontinuum source is used in place of the entire ring cavity laser 26 including tunable filter 16. A wide-band short pulse of a supercontinuum source, having for example an output spectrum spanning a wavelength range from 1,200 nm to 1,550 nm, is stretched to a long pulse of 70-ns duration by using a dispersive fiber due to the group-velocity dispersion and can be used directly as a swept source.

Figure 13:
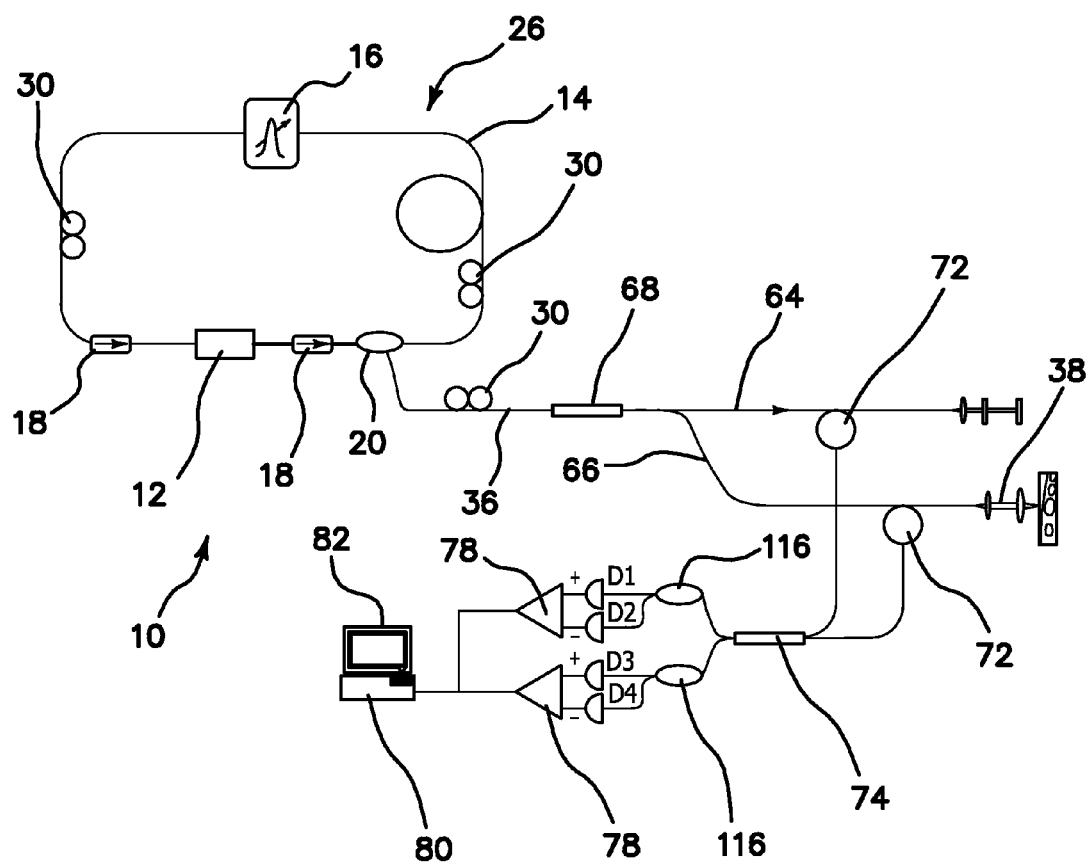
FIG. 13 is a schematic diagram of a narrow line-width swept-source based on a FP tunable filter and WDM couplers.

Another embodiment is schematically depicted in FIG. 13 where a high speed narrow bandwidth wavelength swept source based on a Fabry-Pérot (FP) tunable filter and wavelength-division multiplexing (WDM) couplers is illustrated. As shown in FIG. 13 the swept source 10 of FIG. 1 has its output 36 coupled to the reference arm 64 and sample arm 66 of the interferometer 60 similar to that described below in FIG. 9, but the interference signal from coupler 74 is instead sent to WDM couplers 116. As a tunable filter 16 works at multi-band mode, two or more wavelengths working at different spectral bands are filtered out simultaneously. The spacing between the adjacent spectral bands is determined by the free spectral range (FSR) of the filter 16. As a result, the output light from the swept source 10 is comprised of multi wavelengths which scan within different spectral bands respectively. In the detection arm 76 of the swept source OCT system 60, two or more WDM couplers 116 pass-band match the spectral bands of the filter 16. Consequently the interference signals in different spectral bands are divided into separate channels for detection. Each of the detected channels are separately differentially amplified and combined digitally in computer 82 after analog to digital conversion. Narrow linewidth of the output light from the swept source 10 can be achieved thanks to the small tuning range within each spectral band, while high axial resolution of the system can still be obtained since the total scanning range combining multi bands is broad.

Figure 2:
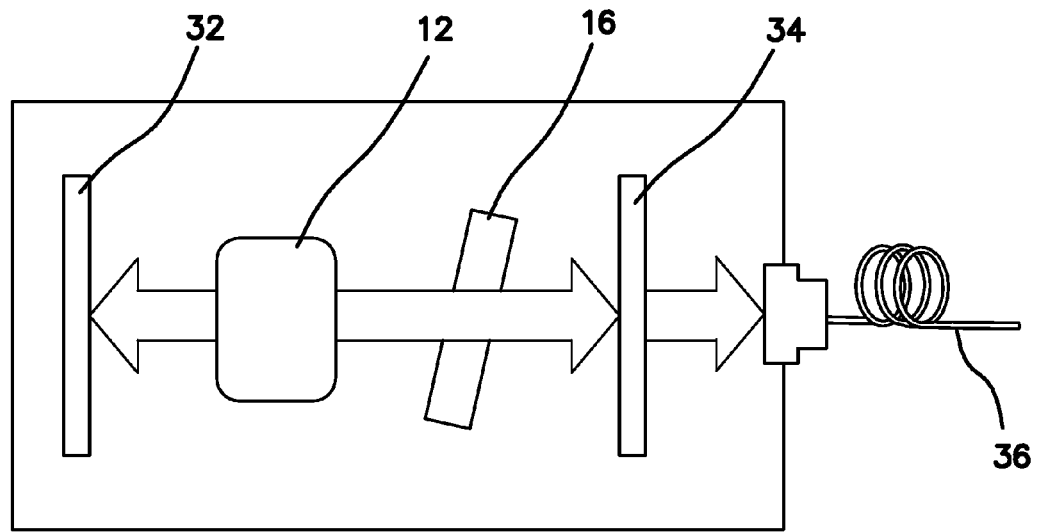
FIG. 2 is a schematic of a prototype setup of the narrow line-width swept-source based on a short cavity.

Consider now another embodiment of a high speed narrow bandwidth wavelength swept source 10 based on a short cavity 28 as shown in FIG. 2. The swept source 10 incorporates a high gain module 12, a tunable narrow bandwidth bandpass filter 16 and the associated reflector 32 and partial reflector 34 to form a short cavity laser 28, whose output is coupled to a fiber 36. The cavity length is in the order of centimeters or millimeters. The gain module 12 can be provided by semiconductor optical gain chips, or gain medium originated from nonlinear effects. The typical nonlinear effects include stimulated Raman scattering (SRS), four wave mixing (FWM), or stimulated Brillouin scattering (SBS) etc.

Figure 14:
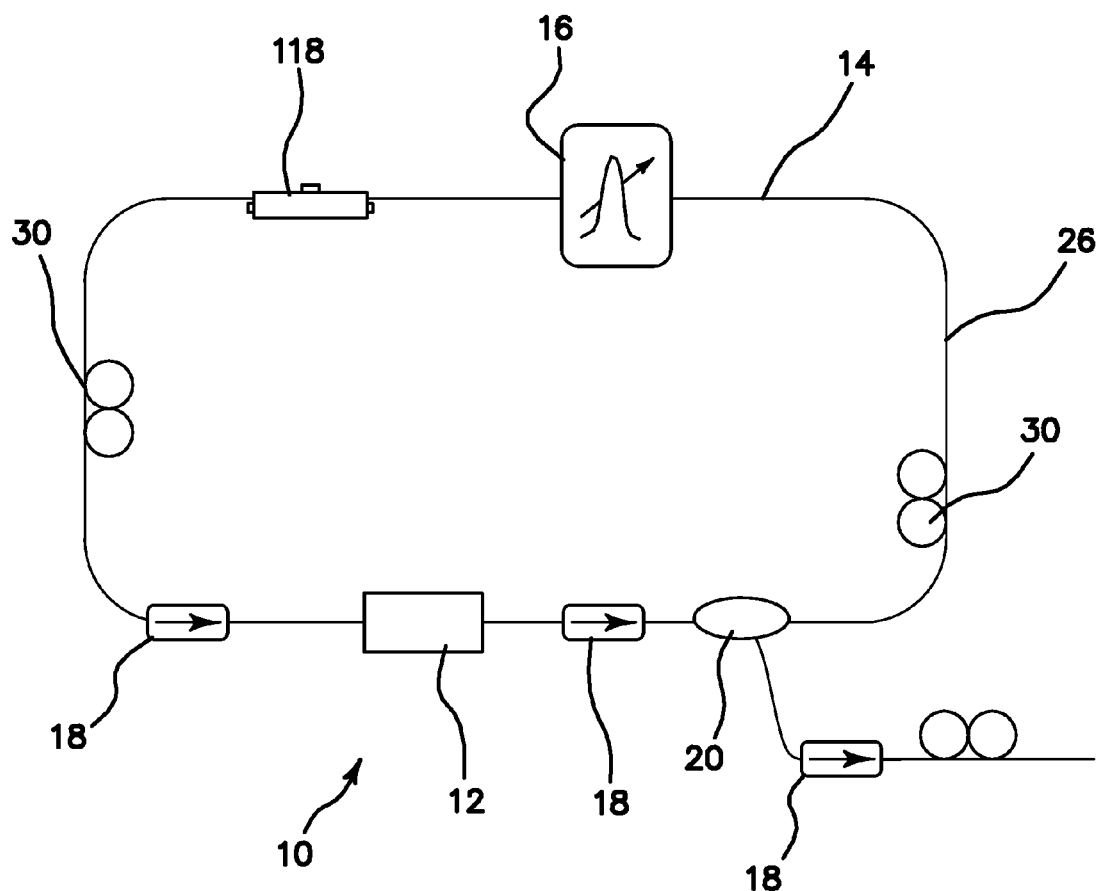
FIG. 14 is a schematic diagram of a narrow line-width swept-source based on a frequency shifter.

In another embodiment as shown in the diagram of FIG. 14, the swept source 10 incorporates a high gain module 12, a fiber coil 14, a tunable narrow bandwidth bandpass filter 16, a frequency shifter 118 and the associated optical isolators 18 and couplers 20 to form a unidirectional ring laser 26. The shifted frequency generated by the frequency shifter 118 is chosen to be identical to the scanned frequency of the tunable filter 16 over the round-trip time of light in the cavity. The laser modes working at the peak wavelength of the filter 16 will always experience the minimum loss as the filter 16 is scanned and can travel many round trip cycles in the cavity. Hence the line-width of the light is significantly narrowed.

It can be seen that the forward scanning (increasing wavelength) and the backward scanning (decreasing wavelength) have the same intensity profile and peak power since the laser operates in a quasi-stationary regime. This is one advantage of the embodiment of FIG. 1 over a short cavity swept laser in which the backward scan profile is degraded at a high scan rate. This symmetry allows OCT imaging to use both the forward and backward swept cycles thereby doubles the imaging speed.

Current commercial swept-sources suffer from the limitation of a maximum tuning rate due to the characteristic time constant required for building up laser activity inside the cavity. In addition, spectral line width of the swept-source is broad since the minimum line width is proportional to the tuning rate with this technique. This limitation can be overcome with the disclosed FDML technique by extending the laser cavity and periodically driving the optical bandpass filter synchronously with the optical round-trip time of the propagating light wave in the cavity. This permits unprecedented sweep rates and broad sweep ranges. In addition, narrow instantaneous line width can be achieved because FDML swept-source operates in a quasi-stationary regime, which will allow the long imaging depths needed for long-range anatomical OCT in sleep apnea evaluation. Although high speed FDML has been demonstrated, the imaging depth of reported FDML swept-source FDOCT systems up to this time is less than 7 mm. The disclosed swept laser source 10 based on FDML technique has the following design parameters: 1) Instantaneous line width will be narrower than 0.04 nm achieves long imaging range required; 2) Real-time in-vivo detection and three dimensional imaging with a high scanning speed approximately 50 kHz. When both forward scanning and backward scanning are used, 100 kHz A-scan can be achieved at scanning rate of 50 kHz; 3) Source power of more than 10 mW to obtain high signal to noise ratio.

The line width of a FDML swept-source 10 is determined by the spectral bandwidth of the intracavity tunable filter 16 and the dispersion of the resonator material of fiber 14. If there is dispersion in the resonator material of fiber 14, the round trip time delay of different wavelength components in the cavity will not be identical. The time delay mismatch between the longest and shortest wavelengths of the scanning spectrum is given by $$\tau_m = dL\Delta\lambda_{tuning} \quad (2)$$

where d is the linear dispersion coefficient of the single mode fiber, L is the fiber length and $\Delta\lambda_{tuning}$ is the tuning bandwidth of the FDML swept-source. For FDML operation, this time mismatch must be smaller than the time duration $\tau_{gate}$ the for the bandpass tunable filter to transmit a single wavelength. With the filter bandwidth $\delta\lambda$, filter driven frequency f and a duty cycle factor $\eta$, $\tau_{gate}$ can be calculated as $$\tau_{gate} = \frac{\eta \cdot \delta\lambda}{f \cdot \Delta\lambda_{tuning}} \quad (3)$$

The condition of $\tau_m < \tau_{gate}$ requires:

$$\delta\lambda > \delta\lambda_m = \frac{f \cdot \Delta\lambda_{tuning}^2 \cdot dL}{\eta} = \frac{c \cdot d \cdot \Delta\lambda_{tuning}^2}{n\eta} \quad (4)$$

where c is the velocity of light and n is the refractive index of the optical fiber. Equation (4) shows that the minimum line width of a FDML swept-source, if permitted by the bandwidth of the tunable filter 16, is proportional to the linear dispersion coefficient and square of tuning bandwidth, independent of scanning frequency.

Figure 7:
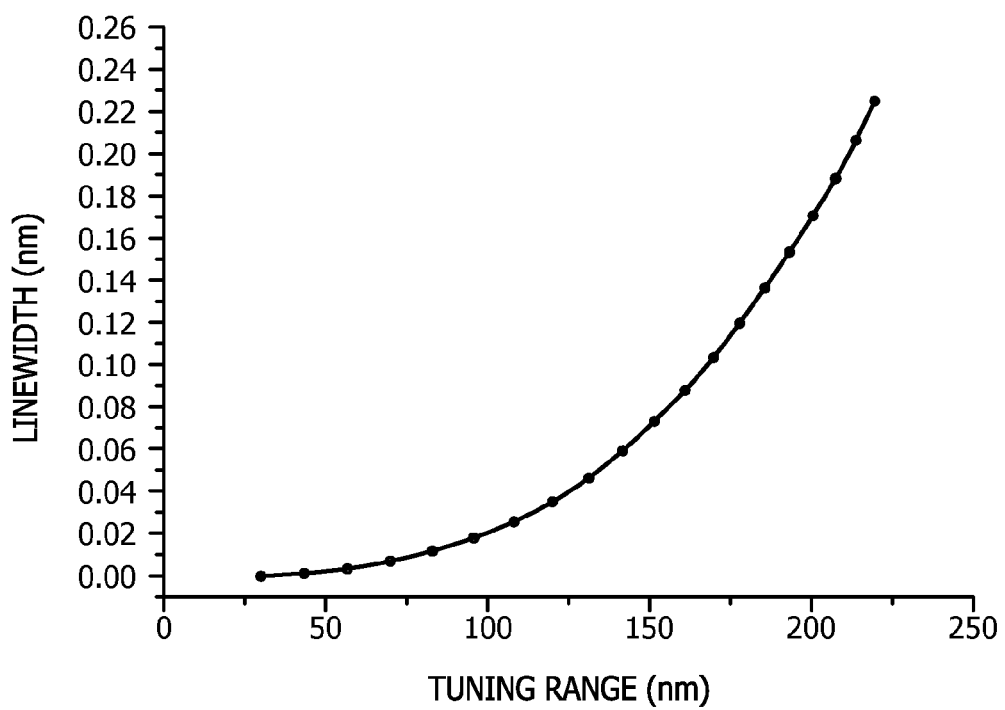
FIG. 7 is a graph of the minimum line width versus tuning range of a swept-source at center wavelength around zero dispersion point of the single mode fiber.

The linear dispersion of a standard single mode fiber 14 is minimum around wavelength of 1310 nm. Considering the residual second order dispersion with dispersion slope of 0.089 ps/(nm² km), the minimum line width with different tuning range can be calculated as shown in FIG. 7.

To achieve a narrow line width, we 1) adjust the center wavelength of the swept-source to the zero dispersion point of the single mode optical fiber (d=0) by tuning the bias voltage of the FFP-TF 16 driven signal, 2) set the tuning range to be less than 80 nm by selecting a SOA 12 with appropriate spectrum, and 3) use a tunable filter 16 with a narrow line width of 0.03 nm.

Due to the mechanical tuning of the filter 16, the proposed swept-source 10 will experience potential spectrum drift during lengthy operation. The alternative solutions include 1) deploying a wavelength reference technique to stabilize swept spectrum by use of a feedback signal to control and maintain the filter bias at the same starting wavelength, and 2) applying a scanning filter strategy based on a non-mechanical tuning mechanism such as electro-optic or acoustic-optic techniques discussed above.

Endoscopic Probes

Figure 3:
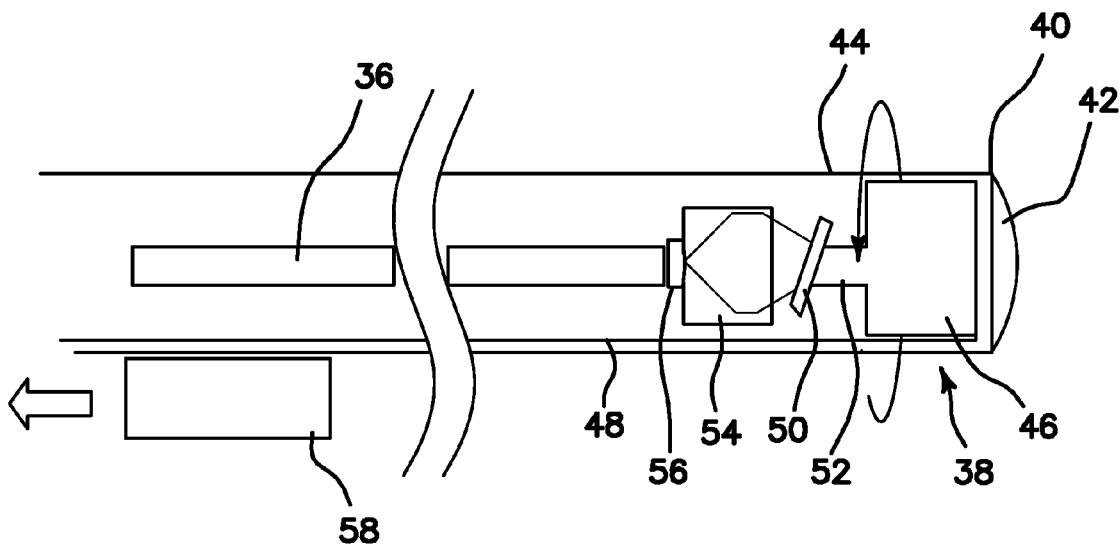
FIG. 3 is a schematic of the OCT probe of the illustrated embodiments with a long working distance.

We have further developed various endoscopic probes 38 for OCT using MEMS and MEMS motors 46. Consider further the use of a micro motor based endoscopic probe 38 as shown in FIG. 3. The distal end 40 of the OCT probe 38 is enclosed by a round-shaped medical ultraviolet glue termination 42 to reduce tissue damage when the probe 38 is advanced into internal organs. Inside the biocompatible FEP tube comprising the probe housing 44, a micro MEMS motor 46 is backwardly mounted at the distal end 40 of the probe 38 and is driven by an outside motor controller (not shown) through a control wire 48 coupling the controller to motor 46. A mirror 50 is glued at the tip of the output shaft 52 of the MEMS motor 46 to reflect the beam which is focused by a GRIN lens 54 toward the sample. A glass rod spacer 56 is placed between the optical fiber 36 and the GRIN lens 54 to reduce the strong reflection from the surface of the GRIN lens 54. Probe 38 is coupled to a translational stage 58 to provide precisely controlled longitudinal displacements of probe 38. The outer diameter of the entire endoscope package is 3 mm.

The illustrated embodiments of the invention provide a cost-effective and direct modality for diagnosis of obstructive sleep apnea by dynamically determining the sites and extent of airway collapse during obstructive sleep apnea. This technology should also provide a method for determining when continuous positive airway pressure (CPAP) or other treatments have been optimized, and for mapping out sites for surgical intervention in surgical sleep apnea treatment candidates.

The major advantage of the MEMS motor based endoscope 38 is that the coupling of rotation torque from the proximal end of the traditional endoscope is not necessary. Since the need for a rotating actuator wire running the entire length endoscope rotation is eliminated, the metal sheath to reinforce the actuator and optical fiber over the length of the probe in previous rotating flexible fiber optic endoscope probe designs is not needed. This leads to increased endoscope flexibility and performance at complex probe bending angles required for airway imaging.

In addition, the fiber rotator joint between the traditional rotational endoscope and static sample arm fiber in the OCT interferometer is not used, which decreases coupling power fluctuation seen in traditional probe designs.

Compared with a linear scanning probe, a rotational scanning probe 38 has the advantages of much higher scanning speed and the capability of screening the whole cross section of a circular organ. As disclosed we have developed a rotational scanning probe 38 based on MEMS technology that allows three dimensional imaging. This design improves endoscope flexibility and stability by eliminating the entire probe length actuator wire rotation utilized in a traditional rotational endoscope. In addition, fluctuation of power coupling into the probe 38 is reduced since a rotating optical coupling joint is not required at the proximal end. The high speed MEMS rotational motor based endoscopic probe 38 meets the following design parameters: 1) Rotating speed is at least 100 circles/s for real-time imaging; 2) Working distance is more than 12 mm for imaging over 30 mm. The diameter of the MEMS motor 46 is 1.5 mm and the outer diameter of the flexible endoscope packaged inside a biocompatible FEP tube is 2.2 mm. Because the micro motor 46 is the sole moving part in achieving a full 360 degrees circular view, high speed circumferential scanning (100 rotations/second) can be achieved easily.

Figure 8:
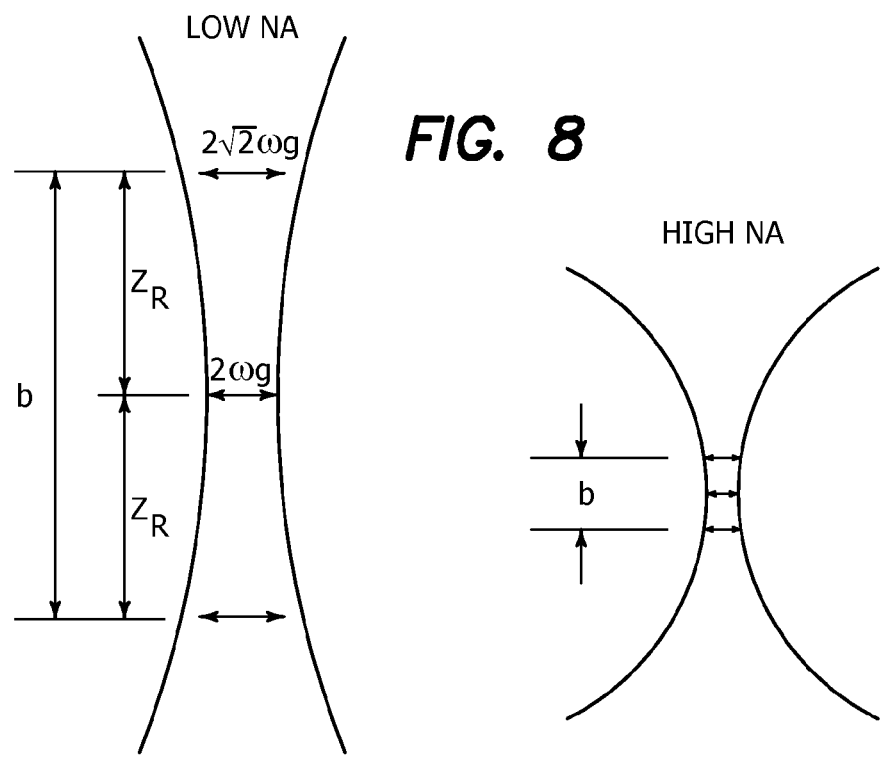
FIG. 8 is a diagram illustrating the effect of lateral resolution and depth of field for OCT focus fiber optic lens systems. Decreased NA improves depth of field, with lateral resolution depressed.

The depth of field (DOF) of the probe optics should be large enough to maintain high signal to noise ratio over the long-range. As schematically shown in FIG. 8, DOF of a lens system is determined by the focal spot as:

$$b = \frac{\pi \Delta x^2}{2\lambda} \quad (5)$$

where $\Delta x = 2\omega_0$ is the spot size, and $\lambda$ is the wavelength. With a low numerical aperture (NA) focusing, the lateral resolution of the probe is designed to be 200 μm which is high enough for determining size and shape of a large hollow organ. The corresponding DOF will be 50 mm.

Imaging artifacts due to back reflection can be suppressed significantly. For imaging a range from 3 mm to 30 mm, the working distance of the proposed probe 38 is designed to be 12 mm by selecting a long focal length GRIN lens 54. The working distance of the probe 38 and focal spot can be tuned precisely by adjusting the length of the glass rod spacer 56. Angular velocity of the motor 46 is provided with a cycle feedback control, which is advantageous for synchronization in three dimensional slice image acquisition. In addition, the probe 38 uses a lightweight mirror 50 instead of a micro reflecting prism to reflect the focusing beam which is easier to package. A high speed linear motor 58 outside the endoscope pulls back the entire probe 38 within a stationary sheath with a linear movement range of 15 cm and speed of up to 20 cm/s to create a three dimensional helix scan as schematically. The helix pitch of 2 mm will not provide dense imaging of the whole inner surface of the target. However it is more than enough resolution for imaging the upper airway profile for sleep apnea determination applications.

The entire probe 38 is designed to move within a stationary transparent protective biocompatible sheath 44 with outer diameter of 3 mm which allows the probe 38 to move longitudinally without being sensed by the patient. With linear motion speeds of 20 cm/s, it will take less than 1 second for the probe to scan over a 15 cm long upper airway.

Figure 6A:
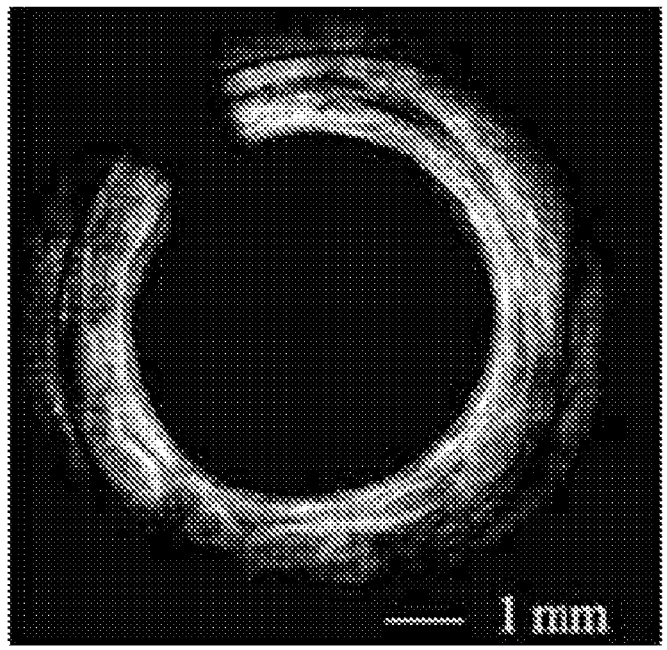
FIGS. 6a and 6b are three dimensional OCT images of in-vivo human left lower lobe bronchus. The longitudinal length is 8 mm.
Figure 6B:
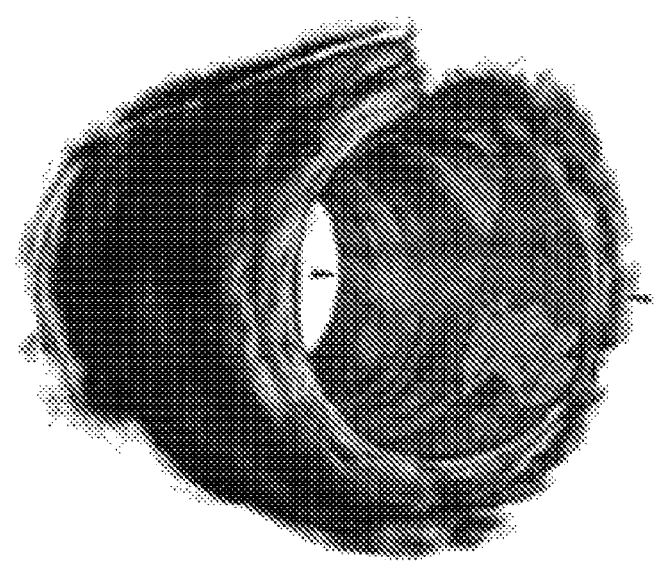

Consider now a reduction to practice with an example of in-vivo human airway OCT imaging. FIGS. 6a and 6b show three dimensional in-vivo image of human left lower lobe bronchus with an endoscopic FDOCT operated at the imaging speed of 20 frames per second (fps). A lesion at inside wall surface of the trachea can be clearly identified.

In summary, it can be understood that the illustrated embodiment includes a fast scanning (50 kHz) swept laser source 10 with a line width of 0.04 nm based on FDML techniques. The swept-source FDOCT system has an imaging range of at least 35 mm. A MEMS micro motor based endoscopic probe 38 is capable of helical scanning with rotating speed of 100 revolutions per second and linear moving speed of 20 cm per second respectively. The imaging processing and data analysis algorithms employed in a conventional computer provide real-time quantification of upper airway anatomy.

FDOCT Integrated System

The one way and repetitive linear sweep movement of the probe 38 over 15 cm length will take less than one second (pull back) and a 2-3 of seconds (advancement), respectively. The scanning speed is acceptable for imaging apnea which typically lasts more than 10 seconds. However, in another embodiment probe 38 can be provided with distributed multiple imaging heads which focus multiple beams to the target to improve the performance significantly if such capabilities are needed for other special clinical applications.

Figure 9:
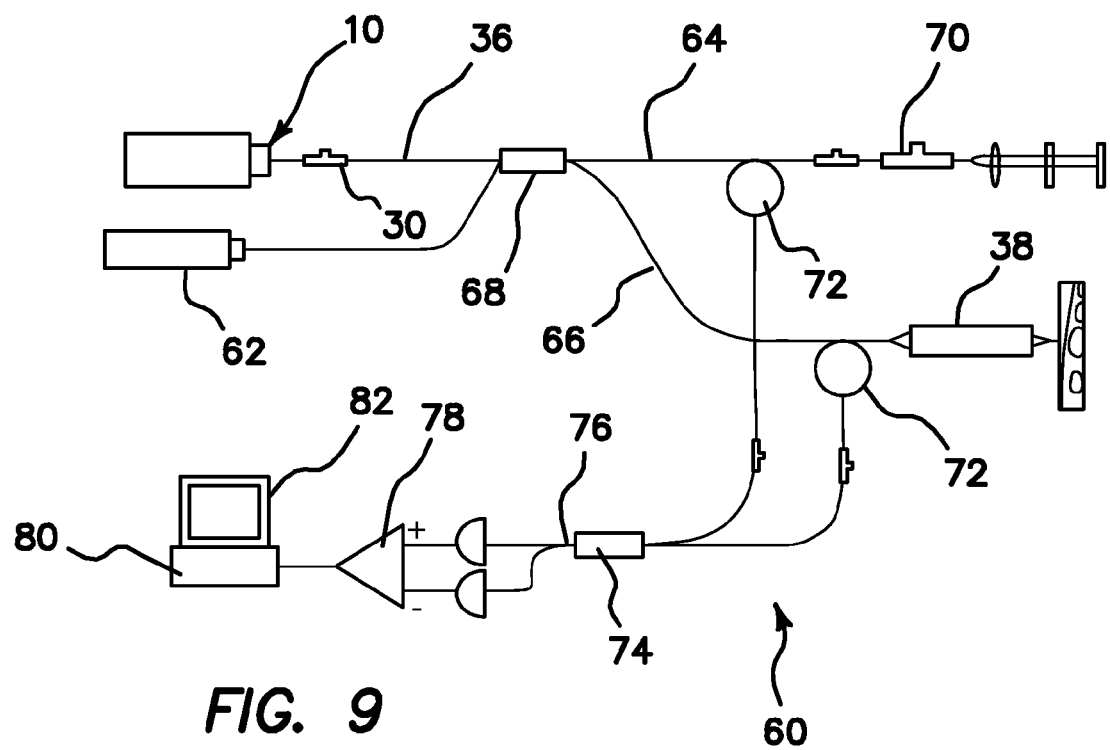
FIG. 9 is a schematic diagram of the entire long-range swept-source FDOCT system of the illustrated embodiment.

The proposed integrated high speed long-range swept-source FDOCT system 60 is shown in FIG. 9. The FOOCT system 60 includes a fiber optic Michelson interferometer with a FDML swept light source 10. A green visible aiming laser 62 is used to demarcate the area scanned. Subsequently, the light is split into reference arm 64 and sample arm 66 of the optic Michelson interferometer by a 2×2 coupler 68. In the reference arm 64, a polarizing electro-optic (EO) phase modulator 70 is used to generate a stable carrier frequency for heterodyne detection. This technique enables doubling the imaging range by canceling the overlapped mirror images and improvement of SNR by eliminating the autocorrelation noise close to the zero position. Two circulators 72 are used in both the reference arm 64 and sample arm 66 to redirect the back-reflected light to a 2×2 fiber coupler 74 (50/50 split ratio) for balanced detection. The proximal end of the endoscopic probe 38 is connected to the sampling arm 66. In the detection arm 76, the fringe signal collected by the photodetectors 78 is differentially amplified by amplifier 78 converted by a high speed PCI Express data acquisition board 80 and transferred to a computer 82 for processing. A trigger signal is generated by the swept-source 10 to initiate the data acquisition process for each A-line. Longitudinal movement of the probe 38 is controlled by the computer 82. The position, moving range, speed and time can be set accurately for various working modes including single cycle scanning, short term scanning, continuously scanning and moving to a particular location etc.

The FDOCT system 60 can speed up data acquisition to 100 K lines of raw data (i.e. the detected electrical signal) in one second when both forward and backward scanning are used. At a setting of 200 μm spacing, the setup can obtain 100 frames/second for 200 mm lateral spans corresponding to a circumferential scan with radius of 30 mm. The 0.04 nm line width of the swept-source permits an imaging range of 18 mm. With the mirror image removed with the EO modulator 70, the imaging range of the proposed system is more than 35 mm.

Axial resolution ($\Delta z$) of the FDOCT system 60 is governed by the source center wavelength ($\lambda$) and the FWHM bandwidth ($\Delta \lambda$):

$$\Delta z = \frac{2\ln 2}{\pi} \cdot \frac{\lambda^2}{\Delta \lambda} \quad (6)$$

The FWHM bandwidth of the FDML swept-source is 30 nm, thus the corresponding axial resolution of the proposed FDOCT system 60 will be 25 μm. As discussed above in detail, the lateral resolution of 200 μm is determined by the sampling probe optics.

Figure 10:
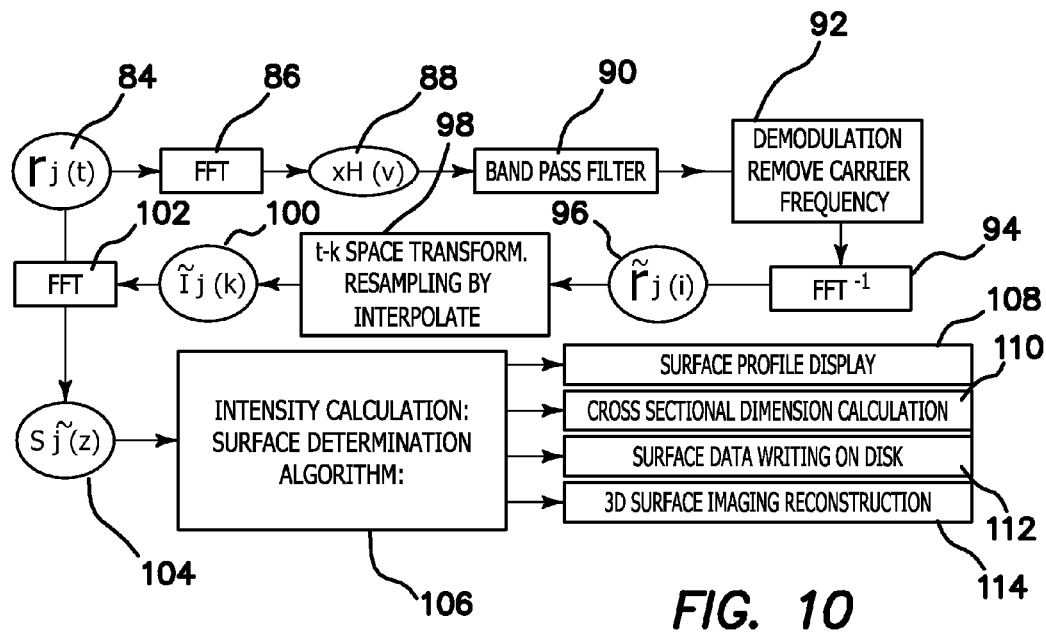
FIG. 10 is a flow diagram of the signal processing procedures used in the computer of FIG. 9.

The imaging processing procedures for FDOCT based on a swept-source can be understood by viewing FIG. 10, where FFT denotes the fast Fourier transform, FFT$^{-1}$ denotes the inverse fast Fourier transform, x is a multiplying symbol, H(v) is the Heaviside function given by:

$$H(v) = \begin{cases} 0 & v < 0 \\ 1 & v \geq 0 \end{cases} \quad (7)$$

The two dimensional structural image is converted to polar coordinate and displayed at the rate of 100 fps. The cross sectional dimension in one circumferential scan calculated with the surface location is displayed in real-time at 100 points per second at step 110. These real-time images and plots help physicians to identify open and obstructed regions of the upper airway. All the data of surface location will be recorded on the hard drive in real-time at step 112. For three dimensional imaging display, we have developed our own three dimensional image processing algorithm by post processing the recorded data at step 114. The physician can pick up one or several cycles during screening to reconstruct the three dimensional volume images right away, or choose any scanning cycles to rebuild three dimensional volume images based on the saved data after the entire overnight study is finished.

For correlation with the standard polysomnography measurement, absolute time of the scans should be known relative to the concurrent polysomnogram. This can be accomplished either with a standard time clock such as the calibrated internal clock of the computer or an Internet time base or synchronizing with the time clock providing by the polysomnography equipment.

With 100 K data points generated in one second, the dataset of surface location for one hour study will occupy 400 MB storage space. A mass storage drive with capacity of more than 4 GB is required to store the data for overnight study. Such storage requirements are readily accommodated inexpensively at this time with standard mass storage devices.

Figure 11:
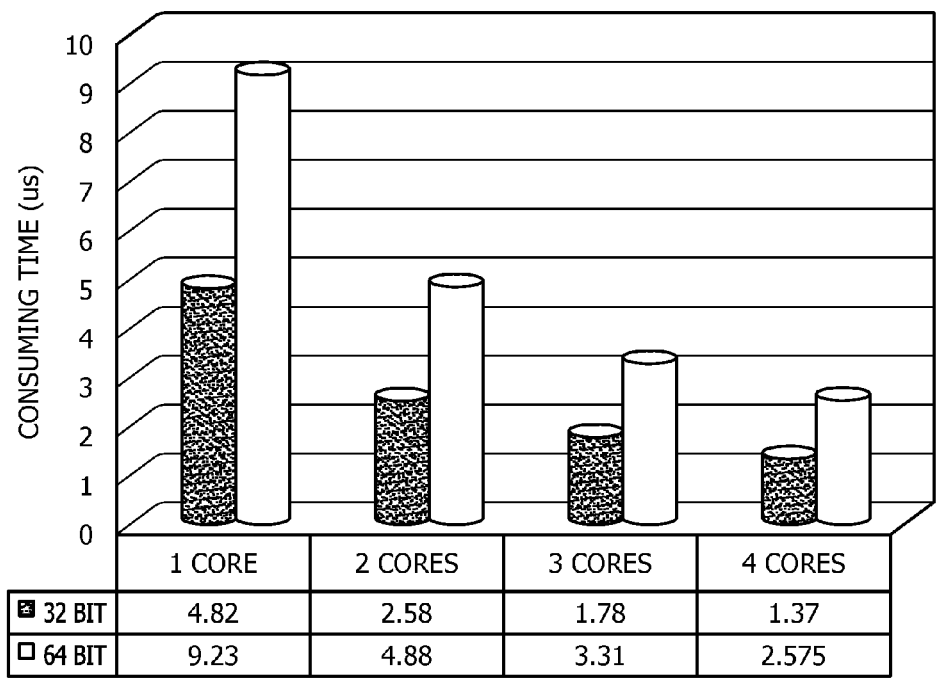
FIG. 11 is a graph of the consuming time for 1024 point complex FFT processing with different number of cores.
Figure 12:
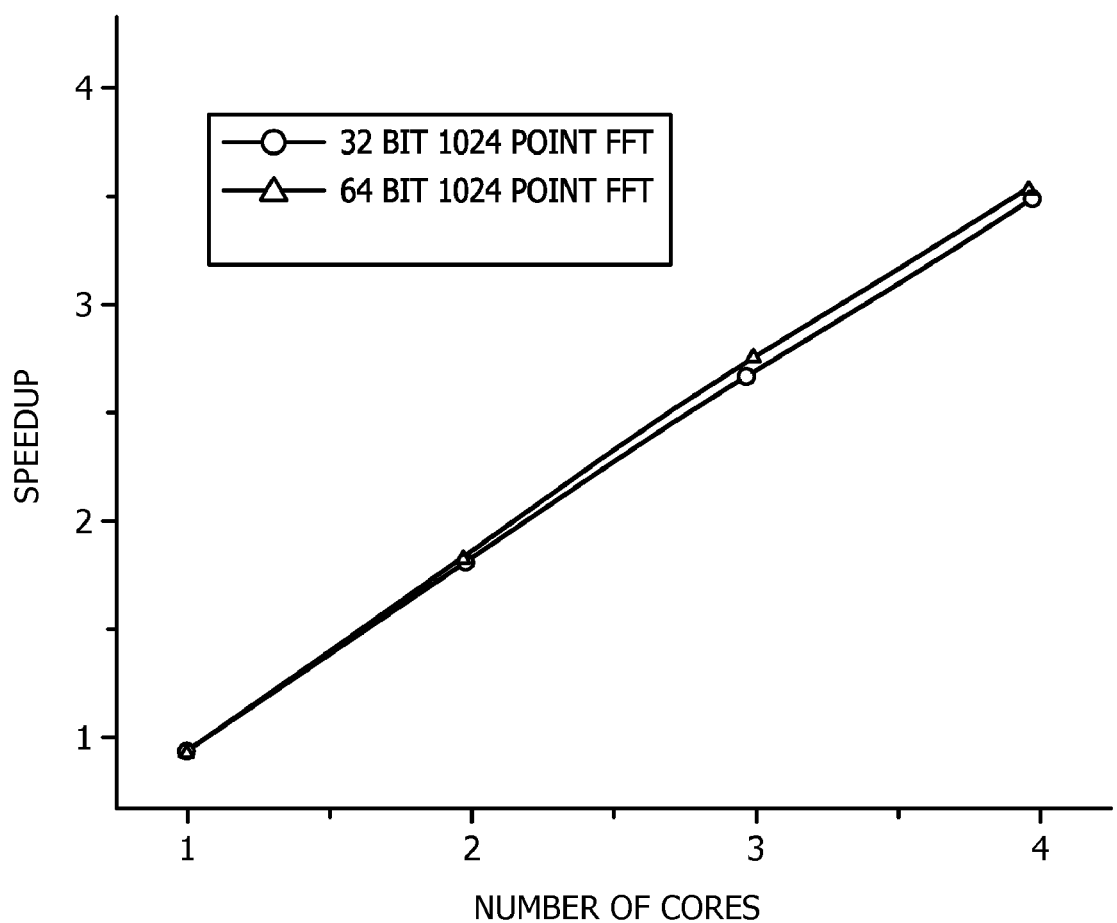
FIG. 12 is a graph of the speed-up with multi-cores in comparison to one core.

Parallel computing is used for real-time processing. The increased incoming data flow, multiple FFT calculations, real-time surface profile display and cross sectional dimension plotting requires high grade processing capabilities. Post processing is the typical method for high speed OCT imaging which compromises real-time monitoring. We use a shared memory parallel computing processing engine to yield 100K processed lines per second for real-time imaging. Most personal computers are prebuilt with multiple processing units such as multi-core CPUs and multi-core video processors. With these multiple processing units, high performance parallel computing can be adapted to significantly increase the processing speed without inclusion of additional hardware. The speed-up of parallel computing can be described by Amdahl's law:

$$\text{speedup} = 1/(1 - P + P/N) \quad (8)$$

Where P is the ratio of the parallel part to the whole task. N is the number of processing units. If the whole task can be parallelized (P=1), the speed-up will be proportional to the number of processing units. In our current OCT configuration, a shared-memory parallel computing technique is used for data acquisition and processing based on a quadruple core processor computer. FIG. 11 shows the consuming time of 1024 point complex FFT calculation by use of our parallel computing method with different number of cores turned on. The speed-up with multi-cores in comparison to one core shown in FIG. 12 confirms the linear relationship of speed-up with number of processing units. With our parallel computing algorithm, a quadruple core system is capable of 3.6 times faster processing than one core system.

We tested our code for data acquisition and imaging processing of swept-source FDOCT systems 60. The software with current quadruple core computer could provide real-time acquisition and processing ability for a FDOCT system with A-line rate of up to 80 kHz.

We use a computer with an octuple core processer for processing and display. A much higher processing speed is expected according to equation (8). In combination with a PCI Express data acquisition board 80 which provides four times the data streaming rate compared with conventional PCI bus boards, we will be able to achieve real-time processing and data acquisition for the proposed 100 kHz long-range FDOCT system 60.

Many alterations and modifications may be made by those having ordinary skill in the art without departing from the spirit and scope of the invention. Therefore, it must be understood that the illustrated embodiment has been set forth only for the purposes of example and that it should not be taken as limiting the invention as defined by the following invention and its various embodiments.

For example,

Therefore, it must be understood that the illustrated embodiment has been set forth only for the purposes of example and that it should not be taken as limiting the invention as defined by the following claims. For example, notwithstanding the fact that the elements of a claim are set forth below in a certain combination, it must be expressly understood that the invention includes other combinations of fewer, more or different elements, which are disclosed in above even when not initially claimed in such combinations. A teaching that two elements are combined in a claimed combination is further to be understood as also allowing for a claimed combination in which the two elements are not combined with each other, but may be used alone or combined in other combinations. The excision of any disclosed element of the invention is explicitly contemplated as within the scope of the invention.

The words used in this specification to describe the invention and its various embodiments are to be understood not only in the sense of their commonly defined meanings, but to include by special definition in this specification structure, material or acts beyond the scope of the commonly defined meanings. Thus if an element can be understood in the context of this specification as including more than one meaning, then its use in a claim must be understood as being generic to all possible meanings supported by the specification and by the word itself.

The definitions of the words or elements of the following claims are, therefore, defined in this specification to include not only the combination of elements which are literally set forth, but all equivalent structure, material or acts for performing substantially the same function in substantially the same way to obtain substantially the same result. In this sense it is therefore contemplated that an equivalent substitution of two or more elements may be made for any one of the elements in the claims below or that a single element may be substituted for two or more elements in a claim. Although elements may be described above as acting in certain combinations and even initially claimed as such, it is to be expressly understood that one or more elements from a claimed combination can in some cases be excised from the combination and that the claimed combination may be directed to a subcombination or variation of a subcombination.

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements.

The claims are thus to be understood to include what is specifically illustrated and described above, what is conceptionally equivalent, what can be obviously substituted and also what essentially incorporates the essential idea of the invention.

We claim:

1. An endoscopic swept-source Fourier Domain optical coherence tomographic system (FDOCT system) for imaging of tissue structure comprising:
    a Fourier Domain mode locked (FDML), high speed, narrow line-width, wavelength swept source;
    an OCT interferometer having a sample arm, a reference arm, a detection arm, and a source arm coupled to the swept source;
    an endoscopic probe coupled to the sample arm; and
    a data processing circuit coupled to the detection arm,
    where the swept source comprises a long single mode optic fiber functioning as a cavity, a high optical gain lasing module, and a tunable narrow bandwidth bandpass filter for wavelength selection combined to form a unidirectional ring laser cavity, driven synchronously with the optical round-trip time of a propagating light wave in the cavity, and operating, where the tunable filter operates in a multi-band mode by simultaneously filtering two or more wavelengths at different spectral bands so that the swept source has an output comprised of multi wavelengths within different spectral bands and further comprising at least two wavelength-division multiplexing (WDM) couplers in optical circuit in the detection arm of the OCT interferometer, where the WDM couplers pass-band match the spectral bands of the filter and where the OCT interferometer divides the spectral bands into separate channels for detection.

2. The FDOCT system of claim 1 where the swept source is arranged and configured to operate in a quasi-stationary regime.

3. The FDOCT system of claim 1 where the swept source has a center frequency adjusted to the zero dispersion point of a single mode optical fiber by tuning the bias voltage of a filter driven signal, where the tuning range of the filter is set to less than 80 nm by using a gain medium with a predetermined spectrum relative to the bandwidth response of the tunable filter, and arranging and configuring the tunable filter to have a line width of not more than approximately 0.03 nm.

4. The FDOCT system of claim 3 further comprising means for deploying a multi-wavelength reference to stabilize a swept spectrum by using a feedback signal to control and maintain the tunable filter bias at a starting wavelength, and means for applying a scanning filter strategy based on a non-mechanical tuning mechanism.

5. The FDOCT system of claim 1 where the endoscopic probe comprises:
    a hollow elongate flexible sheath with a distal and proximal end;
    an optic fiber extending from the proximal toward the distal end of the sheath,
    a GRIN lens coupled to the optic fiber:
    a MEMS motor proximately disposed within the distal end of the elongate sheath and backwardly mounted at the distal end of the sheath and having an output shaft;
    a controller coupled to the motor;
    a flexible control wire coupling the motor and controller extending through the sheath from its proximal end to the motor; and
    a mirror coupled to the output shaft of the motor to reflect the beam which is focused by the GRIN lens toward the mirror and thence to the tissue structure being san pled.

6. The FDOCT system of claim 5 further comprising a glass rod spacer disposed between the optic fiber and the GRIN lens to reduce reflection from the surface of the GRIN lens.

7. The FDOCT system of claim 5 further comprising a translational stage coupled to the sheath to provide precisely controlled longitudinal displacement of the sheath.

8. The FDOCT system of claim 5 where the GRIN lens is arranged and configured to have a long focal length so that the probe imaging range is at least from 3 mm to 30 mm within which a working distance lies.

9. The FDOCT system of claim 8 where a glass rod spacer has a length and where the working distance of the probe and its focal spot is precisely tunable by adjusting the length of the glass rod spacer.

10. A method of using an endoscopic swept-source Fourier Domain optical coherence tomographic system (FDOCT system) for rapid three-dimensional anatomical imaging of an airway and for determining the site and extent of airway collapse during obstructive sleep apnea comprising:
    providing a narrow line-width, wavelength swept source;
    Fourier Domain mode locking (FDML) the narrow line-width, wavelength swept source;
    scanning the airway with an endoscopic probe coupled to an OCT interferometer using the swept source as a light source; and
data processing the scanned signal to obtain an image of the airway to determine the site and extent of airway collapse during obstructive sleep apnea,
    where the swept source includes a tunable filter in a cavity, where the cavity is formed as a ring laser cavity using an optical fiber coupled to a gain medium and where operating the swept source in a quasi-stationary regime comprises adjusting a center wavelength of the swept source to a zero dispersion point of the optical fiber by tuning the bias voltage of a filter driven signal, and tuning a wavelength swept range of the filter to less than 80 nm by providing a gain medium with a predetermined spectrum relative to the bandwidth response of the tunable filter, and arranging and configuring the tunable filter to have a line width of not more than approximately 0.03 nm.

11. The method of claim 10 further comprising deploying a multi-wavelength reference to stabilize a swept spectrum by using a feedback signal to control and maintain a tunable filter bias at a starting wavelength.

12. The method of claim 10 further comprising deploying a multi-wavelength reference for spectral calibration by using a Fabry-Perot interferometer, a Mach-Zehnder interferometer or a Michelson interferometer to exhibit uniformly spaced resonance frequency combs.

13. The method of claim 10 further comprising applying a wavelength reference to stabilize a swept spectrum by using a wavelength marker detected by a wavelength filter and using feedback signal to control and maintain the tunable filter and thus wavelength repeatability.

14. The method of claim 10 where Fourier Domain mode locking (FDML) the narrow line-width, wavelength swept source comprises applying a scanning filter strategy using a non-mechanical tunable filter such as an electro-optic or acousto-optic (AO) filter in a ring laser cavity.

15. The method of claim 10 where providing a narrow line-width, wavelength swept source comprises providing spatially dispersed broadband pulses from a supercontinuum source coupled to a dispersive optical fiber as the wavelength swept source.

* * * * *